United States Patent [19]
Fenton et al.

[11] Patent Number: 5,541,219
[45] Date of Patent: Jul. 30, 1996

[54] 1-ALKOXY-2-(ALKOXY- OR CYCLOALKOXY-)-4-(CYCLOTHIOALKYL- OR CYCLOTHIOALKENYL-) BENZENES AS INHIBITORS OF CYCLIC AMP PHOSPHODIESTERASE AND TUMOR NECROSIS FACTOR

[75] Inventors: Garry Fenton; Jonathan S. Mason; Malcolm N. Palfreyman; Andrew J. Ratcliffe, all of Dagenham, United Kingdom

[73] Assignee: Rhone-Poulenc Rorer Limited, Eastbourne, United Kingdom

[21] Appl. No.: 295,747

[22] PCT Filed: Mar. 4, 1993

[86] PCT No.: PCT/GB93/00445

§ 371 Date: Nov. 3, 1994

§ 102(e) Date: Nov. 3, 1994

[87] PCT Pub. No.: WO93/18024

PCT Pub. Date: Sep. 16, 1993

[30] Foreign Application Priority Data

Mar. 4, 1992 [GB] United Kingdom ............. 9204808

[51] Int. Cl.⁶ .................. A61K 31/38; C07D 335/02; C07D 333/02; C07D 333/32
[52] U.S. Cl. .............. 514/432; 514/446; 514/445; 514/438; 514/431; 549/28; 549/13; 549/62; 549/66; 549/67; 549/9; 549/78
[58] Field of Search ................. 549/62, 66, 67, 549/9, 13, 28, 83, 70, 78; 514/438, 446, 432, 431, 445

[56] References Cited

U.S. PATENT DOCUMENTS

| | | | |
|---|---|---|---|
| 2,794,026 | 5/1957 | Johnston | 549/13 |
| 3,558,641 | 1/1971 | Sarett et al. | 549/64 |
| 3,657,432 | 4/1972 | Shen et al. | 549/66 |
| 3,832,354 | 8/1974 | Gadient et al. | 514/64 |
| 3,892,773 | 7/1975 | Allais et al. | 549/13 |
| 4,198,519 | 4/1980 | Goudie | 549/70 |
| 4,757,084 | 7/1988 | Biftu | 549/75 |
| 4,778,819 | 10/1988 | Mishra et al. | 549/77 |
| 5,030,647 | 7/1991 | Miao et al. | 549/70 |
| 5,149,828 | 9/1992 | Rody et al. | 549/13 |
| 5,358,938 | 10/1994 | Cai et al. | |

OTHER PUBLICATIONS

Harrington et al., "Preparation of 3–aryl–2,5–dihydrothiophene–1,1–dioxides from aryl iodides", Tetrahedron Letters, vol. 28, No. 5 (1987), pp. 495–498.

Primary Examiner—José G. Dees
Assistant Examiner—Deborah Lambkin
Attorney, Agent, or Firm—Raymond S. Parker, III; Martin F. Savitzky; James A. Nicholson

[57] ABSTRACT

This invention is directed to 1-alkoxy-2-(alkoxy- or cycloalkyloxy-)-4-(cyclothioalkyl- or cyclothioalkenyl-)benzene compounds that inhibit cyclic AMP phosphodiesterase or tumor necrosis factor (TNF) and are useful in treating patients suffering from disease state capable of being modulated by inhibiting production of cyclic AMP phosphodiesterase or TNF by administering the compound to the patient. The invention is also directed to the preparation of these compounds, pharmaceutical compositions containing these compounds and methods for their pharmaceutical use.

23 Claims, No Drawings

1-ALKOXY-2-(ALKOXY- OR CYCLOALKOXY-)-4-(CYCLOTHIOALKYL- OR CYCLOTHIOALKENYL-) BENZENES AS INHIBITORS OF CYCLIC AMP PHOSPHODIESTERASE AND TUMOR NECROSIS FACTOR

This application is a 371 of PCT/GB93/00445, filed on Mar. 4, 1993.

FIELD OF THE INVENTION

This invention is directed to sulfur-containing aromatic compounds which are useful in inhibiting cyclic AMP phosphodiesterase or tumor necrosis factor. The invention is also directed to the preparation of these compounds, pharmaceutical compositions containing these compounds and methods for their pharmaceutical use.

α-TNF is an important pro-inflammatory glycoprotein cytokine which causes hemorrhagic necrosis of tumors and possesses other important biological activities. α-TNF is released by activated macrophages, activated T-lymphocytes, natural killer cells, mast cells and basophils, fibroblasts, endothelial cells and brain astrocytes among other cells.

The principal in vivo actions of α-TNF can be broadly classified as inflammatory and catabolic. It has been implicated as a mediator of endotoxic shock, inflammation of joints and of the airways, immune deficiency states, allograft rejection, and in the cachexia associated with malignant disease and some parasitic infections. In view of the association of high serum levels of α-TNF with poor prognosis in sepsis, graft versus host disease and acute respiratory distress syndrome, and its role in many other immunologic processes, this factor is regarded as an important mediator of general inflammation.

α-TNF activates neutrophils, eosinophils and endothelial cells to inflammation where they release tissue damaging mediators. α-TNF also activates monocytes, macrophages and T-lymphocytes to cause the production $IL_8$ and GM-CSF, which mediate the end effects of α-TNF. The ability of α-TNF to activate T-lymphocytes, monocytes, macrophages and related cells has been implicated in the progression of Human Immunodeficiency Virus (HIV) infection. In order for these cells to become infected with HIV and for HIV replication to take place the cells must be maintained in an activated state. Cytokines such as α-TNF have been shown to activate HIV replication in monocytes and macrophages. Features of endotoxic shock such as fever, metabolic acidosis, hypotension and intravascular coagulation are thought to be mediated through the actions of α-TNF on the hypothalamus and in reducing the anti-coagulant activity of vascular endothelial cells. The cachexia associated with certain disease states is mediated through indirect effects on protein catabolism. α-TNF also promotes bone resorption and acute phase protein synthesis.

Reported Developments

WO Patent Application No. 92/12961 discloses that a compound of formula

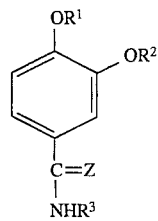

is a cyclic AMP phosphodiesterase inhibitor, but does not disclose or suggest that the compound inhibits TNF.

The object of the present invention is directed to a compound that inhibits TNF and cyclic AMP phosphodiesterase.

SUMMARY OF THE INVENTION

This invention is directed to a novel class of 1-alkoxy-2-(alkoxy- or cycloalkyloxy-)-4-(cyclothioalkyl- or cyclothioalkenyl-)benzene compounds. Compounds within the scope of the present invention inhibit cyclic AMP phosphodiesterase and tumor necrosis factor (TNF) and are useful in treating disease states involving a physiologically detrimental excess of cyclic AMP phosphodiesterase or TNF.

Disease states sought to be treated in accordance with the present invention include inflammatory and autoimmune diseases, pathological conditions attributable to increases in cyclic AMP phophodiesterase (in particular type IV cyclic AMP phosphodiesterase), eosinophil accumulation and the function of eosinophils.

DETAILED DESCRIPTION OF THE INVENTION

As used above, and throughout the description of the invention, the following terms, unless otherwise indicated, shall be understood to have the following meanings:

Definitions

"Patient" embraces both human and other mammals.

The "*" designation on the carbons in the compound according to the invention represents that the carbons are chiral.

"Alkyl" means an aliphatic hydrocarbon group which may be straight or branched having about 1 to about 15 carbon atoms in the chain; preferably about 1 to about 12 carbon atoms in the chain; and more preferably about 1 to about 4 carbon atoms in the chain. Branched means that a lower alkyl group such as methyl, ethyl or propyl is attached to a linear alkyl chain. "Lower alkyl" means about 1 to about 4 carbon atoms in the chain which may be straight or branched. Exemplary alkyl groups include methyl, ethyl, i-propyl, n-butyl, t-butyl, n-pentyl, heptyl, octyl or decyl.

"Cycloalkyl" means a non-aromatic mono cyclic or multi cyclic ring system of about 3 to about 10 carbon atoms. The cyclic alkyl may be optionally partially unsaturated. Preferred cyclic cycloalkyl rings include cyclopentyl, cyclohexyl, cyclohexenyl or cycloheptyl; more preferred is cyclopentyl. Preferred multicyclic cycloalkyl rings include 1-decalin, adamant-(1- or 2-)yl or norbornanyl.

"Cyclothioalkyl" means a monocyclic ring containing about 5 to about 6 members and wherein one of the ring atoms is sulfur. The cyclothioalkyl may be optionally substituted by one or more substituents, which may be the same or different, that include hydrogen, lower alkyl, lower alkoxy, hydroxyl, acyloxy or aroyloxy. The thio moiety of the cyclothioalkyl may be also optionally oxidized to the corresponding S-oxide or S,S-dioxide. Preferred substituents of the cyclothioalkyl include hydrogen, hydroxyl or lower alkoxy.

"Cyclothioalkenyl" means a monocyclic ring containing about 5 to about 6 members and wherein one of the ring atoms is sulfur. The cyclothioalkenyl may be optionally substituted by one or more substituents, which may be the same or different, that include hydrogen, lower alkyl, lower alkoxy, hydroxyl, acyloxy or aroyloxy. The thio moiety of the cyclothioalkyl may be also optionally oxidized to the corresponding S-oxide or S,S-dioxide "Acyl" means an alkyl-CO- group wherein the alkyl group is as previously described. Preferred acyl have an alkyl containing 1 to about 3 carbon atoms in the alkyl group. Exemplary groups include acetyl, propanoyl, 2-methylpropanoyl, butanoyl or palmitoyl.

"Aroyl" means an aryl-CO- group wherein the aryl group is phenyl or naphthyl. Exemplary groups include benzoyl and 1- and 2-naphthoyl.

"Alkoxy" means an alkyl-O- group wherein the alkyl group is as previously described. "Lower alkoxy" means a lower alkyl-O- group wherein the lower alkyl group is as previously described. Exemplary alkoxy groups include methoxy, ethoxy, n-propoxy, i-propoxy, n-butoxy, heptoxy and decoxy.

"Cycloalkyloxy" means an cycloalkyl-O- group wherein the cycloalkyl group is as previously described. Exemplary cycloalkyloxy groups include cyclopentoxy, cyclohexoxy, cyclohexenoxy or cycloheptoxy, 1-decalinoxy, adamant-(1- or 2-)oxy or norbornanoxy.

"Acyloxy" means an acyl-O- group wherein acyl is as defined previously.

"Aroyloxy" means an aroyl-O- group wherein aroyl is as defined previously.

"Halo" mean fluoro, chloro or bromo.

The preferred compounds of the invention are described by formula I

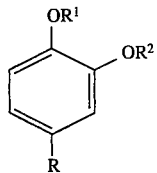

formula I wherein $R^1$ is alkyl;

$R^2$ is alkyl or cycloalkyl group; and

R is cyclothioalkyl or cyclothioalkenyl.

More preferred are the compounds of formula I wherein $R^1$ is lower alkyl and $R^2$ is cycloalkyl of 5 to 7 ring atoms; further preferred is $R^1$ is methyl and $R^2$ is cyclopentyl.

A special embodiment of preferred R subclasses of compounds are cyclothioalkyls depicted by formulae II to IV below

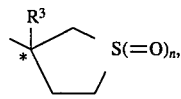

formula II

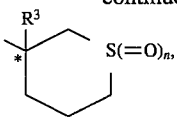

formula III and

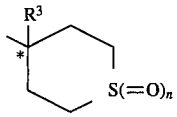

formula IV, wherein $R^3$ is hydrogen, lower alkyl, lower alkoxy, hydroxyl, acyloxy or aroyloxy; and n is 0 to 2, and cyclothioalkenyls depicted by formulae V to IX below

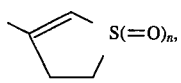

formula V

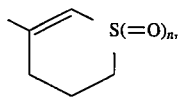

formula VI

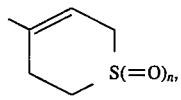

formula VII

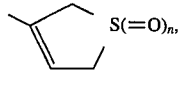

formula VIII and

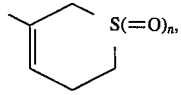

formula IX wherein n is 0 to 2.

More preferred also are the compounds of formula I wherein R is preferably a group of formula II to IV, as described above, wherein $R^3$ is a hydrogen, hydroxy group, lower alkyl or lower alkoxy; and n is 0, 1 or 2.

Preferred are compounds selected from the following:

(A) 4-(3-cyclopentyloxy-4-methoxyphenyl)- 4-hydroxy-3,4, 5,6-tetrahydro-2H-thiopyran;

(B) 4-(3-cyclopentyloxy-4-methoxyphenyl)-t- 4-hydroxy-3, 4,5,6-tetrahydro-2H-thiopyran r- 1-oxide;

(C) 4-(3-cyclopentyloxy-4-methoxyphenyl)- 4-hydroxy-3,4, 5,6-tetrahydro-2H-thiopyran 1,1-dioxide;

(D) 4-(3-cyclopentyloxy-4-methoxyphenyl)- 3,4,5,6-tetrahydro-2H-thiopyran;

(E) 4-(3-cyclopentyloxy-4-methoxyphenyl)- 3,4,5,6-tetrahydro-2H-thiopyran 1,1-dioxide;

(F) cis-4-(3-cyclopentyloxy-4-methoxyphenyl)- 3,4,5,6-tetrahydro-2H-thiopyran 1-oxide;

(G) 4-(3-cyclopentyloxy-4-methoxyphenyl)-c- 4-hydroxy-3,4,5,6-tetrahydro- 2H-thiopyran r-1-oxide;

(H) trans-4-(3-cyclopentyloxy-4-methoxyphenyl)- 3,4,5,6-tetrahydro-2H-thiopyran 1-oxide;

(I) 3-(3-cyclopentyloxy-4-methoxyphenyl)- 3-hydroxy-3,4, 5,6-tetrahydro-2H-thiopyran;

(J) 3-(3-cyclopentyloxy-4-methoxyphenyl)- 3,4,5,6-tetrahydro-2H-thiopyran;

(K) 3-(3-cyclopentyloxy-4-methoxyphenyl)- 3-hydroxy-3,4, 5,6-tetrahydro-2H-thiopyran 1,1-dioxide;

(L) 3-(3-cyclopentyloxy-4-methoxyphenyl)- 3,4,5,6-tetrahydro-2H-thiopyran 1,1-dioxide;

(M) 3-(3-cyclopentyloxy-4-methoxyphenyl)-t- 3-hydroxy-3,4,5,6-tetrahydro- 2H-thiopyran r-1-oxide;
(N) 3-(3-cyclopentyloxy-4-methoxyphenyl)-c- 3-hydroxy-3,4,5,6-tetrahydro- 2H-thiopyran r-1-oxide;
(O) trans-3-(3-cyclopentyloxy- 4-methoxyphenyl)-3,4,5,6-tetrahydro-2H-thiopyran 1-oxide;
(P) cis-3-(3-cyclopentyloxy-4-methoxyphenyl)- 3,4,5,6-tetrahydro-2H-thiopyran 1-oxide;
(Q) 3-(3-cyclopentyloxy-4-methoxyphenyl)- 4,5-dihydrothiophene 1,1-dioxide;
(R) 3-(3-cyclopentyloxy-4-methoxyphenyl)- 3-hydroxy-tetrahydrothiophene 1,1-dioxide;
(S) 3-(3-cyclopentyloxy- 4-methoxyphenyl)tetrahydrothiophene 1,1-dioxide;
(T) 3-(3-cyclopentyloxy-4-methoxyphenyl)- 5,6-dihydro-2H-thiopyran 1-oxide;
(U) 3-(3-cyclopentyloxy-4-methoxyphenyl)- 5,6-dihydro-4H-thiopyran 1-oxide;
(V) 3-(3-cyclopentyloxy-4-methoxyphenyl)- 5,6-dihydro-2H-thiopyran 1,1-dioxide;
(W) 3-(3-cyclopentyloxy-4-methoxyphenyl)- 5,6-dihydro-4H-thiopyran 1,1-dioxide;
(X) cis-3-(3-cyclopentyloxy- 4-methoxyphenyl)-tetrahydrothiophene 1-oxide;
(Y) 3-(3-cyclopentyloxy-4-methoxyphenyl)- 2,5-dihydrothiophene 1-oxide;
(Z) 3-(3-cyclopentyloxy-4-methoxyphenyl)- 4,5-dihydrothiophene 1-oxide;
(AA) 3-(3-cyclopentyloxy-4-methoxyphenyl)- 3-methoxy-3,4,5,6-tetrahydro- 2H-thiopyran 1-oxide;
(AB) 3-(3-cyclopentyloxy-4-methoxyphenyl)- 3-hydroxytetrahydrothiophene;
(AC) 3-(3-cyclopentyloxy-4-methoxyphenyl)- 3-hydroxytetrahydrothiophene 1-oxide;
(AD) trans-3-(3-cyclopentyloxy- 4-methoxyphenyl)tetrahydrothiophene 1-oxide;
(AE) 3-(3-cyclopentyloxy- 4-methoxyphenyl)tetrahydrothiophene;
(AF) 3-(3-cyclopentyloxy-4-methoxyphenyl)- 3-methoxy-3,4,5,6-tetrahydro- 2H-thiopyran;
(AG) (+)-3-(3-cyclopentyloxy- 4-methoxphenyl)tetrahydrothiophene 1,1-dioxide;
(AH) (−)-3-(3-cyclopentyloxy- 4-methoxphenyl)tetrahydrothiophene 1,1-dioxide;
(XA) (+)-cis-3-(3-cyclopentyloxy- 4-methoxphenyl)tetrahydrothiophene 1-oxide; and
(XB) (−)-cis-3-(3-cyclopentyloxy- 4-methoxphenyl)tetrahydrothiophene 1-oxide.

The letters A to XB are allocated to compounds for easy reference in this specification.

Compounds of formula I can be prepared by the application or adaptation of known methods, by which is meant methods used heretofore or described in the literature.

For example, according to a feature of the present invention, a compound of formula I, wherein $R^1$ and $R^2$ are as described above; R is selected from a group of formulae II to IV as described above; $R^3$ is hydroxyl; and n is 0, are prepared by coupling of a compound of formula X

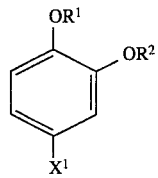

formula X wherein $R^1$ and $R^2$ are as defined above, and $X^1$ is a halo, preferably bromo, with a compound of formula XI

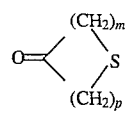

formula XI wherein m is 1 or 2 and p is 2 or 3, such that m+p=3 or 4. A preferred coupling means is the Grignard reaction which is conducted in the presence of magnesium, an ethereal solvent system, such as tetrahydrofuran, and followed by hydrolysis.

According to a further feature of the present invention, a compound of formula I, wherein $R^1$ and $R^2$ are as described above; R is a group of formula IV as described above; $R^3$ is a lower alkyl; and n is 0 is prepared by coupling of a compound of formula X, wherein $R^1$ and $R^2$ are as defined above, and $X^1$ is a halo, preferably iodine, with a compound of formula XII

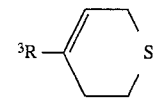

XII wherein $R^3$ is lower alkyl. The coupling may take place in the presence of a triarylphosphine and a palladium salt such as palladium acetate in the presence of a tertiary amine such as triethylamine, at or above about 100° C.

According to a further feature of the present invention, compounds of formula I are prepared by the interconversion of other compounds of formula I.

For example, a compound of formula I, wherein $R^1$ and $R^2$ are as described above; R is selected from a group of formulae II to IV as described above; $R^3$ is hydrogen; and n is 0, are prepared by reducing by known methods a corresponding compounds wherein $R^3$ represents a hydroxy group. Conveniently, the reduction may take place by the action of a silane, e.g. triethylsilane, preferably in the presence of an acid such as trifluoroacetic acid, preferably in an inert solvent such as dichloromethane.

As another example, a compound of formula I, wherein $R^1$ and $R^2$ are as described above; R is selected from a group of formulae II to IV as described above; $R^3$ is hydrogen, hydroxyl or lower alkyl; and n is 1 or 2, is prepared by the oxidizing by known methods of a corresponding compound wherein q is less than desired, e.g., n=0 to n=1 or 2 or n=1 to n=2. Compounds such as sodium periodate are suitable oxidants for the preparation of compounds wherein n is 1. When sodium periodate is used, a suitable solvent system is an aqueous lower alkanoyl, e.g. aqueous methanol. Compounds such as peroxyacids, e.g. 3-chloroperbenzoic acid, or an alkali metal peroxymonosulphate, e.g. potassium peroxymonosulphate, are suitable oxidants for the preparation of compounds wherein n is 2. When a peroxyacid is used, the reaction preferably takes place in an inert solvent, e.g. dichloromethane, preferably near or below room temperature.

As another example, a compound of formula I, wherein $R^1$ and $R^2$ are as described above; R is selected from a group of formulae V to IX; n is 0 to 2, is prepared by dehydrating by known methods a corresponding compound wherein R is a group of formulae II to IV and $R^3$ is hydroxyl. Conveniently, the dehydration may take place in the presence of an acid, e.g. paratoluenesulphonic acid, preferably in the presence of an inert solvent such as acetonitrile, preferably at or near the reflux temperature of the reaction mixture.

As another example, a compound of formula I, wherein $R^1$ and $R^2$ are as described above; R is selected from a group of formulae II to IV as described above; $R^3$ is hydrogen; and n is 0 to 2, is prepared by reducing by known methods a corresponding compound wherein R is selected from a group of formulae V to IX. Conveniently, the reduction may be carried out by means of a reducing agent such as sodium borohydride in the presence of a cobalt (II) salt, e.g. cobalt dichloride, preferably in a solvent such as ethanol, preferably at or near room temperature.

As another example, a compound of formula I, wherein $R^1$ and $R^2$ are as described above; R is selected from a group of formulae II to IV as described above; $R^3$ is lower alkoxy; and n is 1 to 2, is prepared by alkylating by known methods a corresponding compound wherein $R^3$ represents a hydroxyl. For example, the alkylation may be carried out by reacting the hydroxyl compound with a lower alkanoyl in the presence of an acid, e.g. trifluoroacetic acid, preferably at or near room temperature.

As another example, a compound of formula I, wherein $R^1$ and $R^2$ are as described above; R is selected from a group of formulae II to IV as described above; $R^3$ is acyloxy or aroyloxy; and n is 1 to 2, is prepared by acylating by known methods a corresponding compound wherein $R^3$ represents a hydroxyl. For example, the acylation may be carried out by reacting the hydroxyl compound with a acylhalide in the presence of a base, e.g. pyridine, preferably at or near room temperature.

As another example, a compound of formula I, wherein $R^1$ and $R^2$ are as described above; R is selected from a group of formulae II to III as described above; $R^3$ is lower alkyl; and n is 1 or 2, is prepared by reacting a corresponding compound of formula I wherein R is selected from a group of formulae V to VI as described above with a lower alkyl Grignard reagent, in an ethereal solvent system, e.g. tetrahydrofuran, followed by hydrolysis.

As another example, a compounds of formula I, wherein $R^1$ and $R^2$ are as described above; R is selected from a group of formulae II to III as described above; $R^3$ is alkyl; and n is 0, is prepared by the reducing a corresponding compound wherein n is 1 or 2, for example by reaction with lithium aluminum hydride in tetrahydrofuran, at temperature from about room temperature to about 90° C.

It will be apparent to those skilled in the art that certain compounds of general formula I can exhibit isomerism, for example geometrical isomerism and optical isomerism. All isomers within general formula I, and their mixtures, are within the scope of the invention.

Such isomers can be separated from their mixtures, by the application or adaptation of known methods, for example chromatographic techniques and recrystallization techniques, or they may be separately prepared from the appropriate isomers of their intermediates, for example by the application or adaptation of methods described herein.

The starting materials and intermediates can be prepared by the application or adaptation of known methods, for example methods as described in the Reference Examples or their obvious chemical equivalents.

For example, a compound of formula XII, wherein $R^3$ is lower alkyl, may be prepared by dehydrating a compound of formula XIII

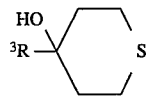

XII wherein $R^3$ is lower alkyl. The dehydration may be carried out by means of an acid, e.g. p-toluenesulphonic acid, preferably in an inert solvent, e.g. acetonitrile, preferably at or near the reflux temperature of the reaction mixture.

Compounds of formula XIII, wherein $R^3$ is lower alkyl, may be prepared by reacting a compound of formula XI, wherein m is 2 and p is 2, with a lower alkyl Grignard reagent, in an ethereal solvent system, e.g. tetrahydrofuran, and followed by hydrolysis.

The present invention is further exemplified but not limited by the following illustrative examples which illustrate the preparation of the compounds according to the invention. The Reference Examples illustrate the preparation of the intermediates.

In the nuclear magnetic resonance spectra (NMR) the chemical shifts are expressed in ppm relative to tetramethylsilane. Abbreviations have the following significance: s=singlet; d=doublet; t=triplet; m=multiplet; dd=doublet of doublets; ddd=doublet of doublets of doublets; dt=doublet of triplets, b=broad.

EXAMPLE 1

Compound A

A suspension of magnesium turnings (0.98 g) in dry tetrahydrofuran (15 mL) is treated with 1,2-dibromoethane (0.2 mL) and the mixture stirred for 40 minutes. A solution of 4-bromo-2-cyclopentyloxyanisole (7 g; which is prepared as described in Reference Example 4) in dry tetrahydrofuran (15 mL), is then added dropwise to the mixture over 10 minutes and then it is heated at reflux for 25 minutes. The mixture is cooled to room temperature, treated with a solution of 3,4,56,6-tetrahydro-2H-thiopyran-4-one (2.5 g) in dry tetrahydrofuran (10 mL), and stirred for 22 hours. The mixture is then treated with saturated aqueous ammonium chloride solution (25 mL) and then with water (100 mL). The mixture is extracted with chloroform ( 2×100 mL) and the combined extracts are dried over sodium sulphate and evaporated, and the resulting residue is subjected to flash chromatography on silica gel, using a mixture of toluene and ethyl acetate (9:1 v/v) as eluent, to give 4-(3-cyclopentyloxy-4-methoxyphenyl)- 4-hydroxy-3,4,5,6-tetrahydro-2H-thiopyran (5.95 g) in the form of a white solid, m.p. 83°–85 ° C. [Elemental analysis: C,66.3; H,7.9; S,10.1%; calculated: C,66.2; H,7.8; S,10.4%].

EXAMPLE 2

Compound D

A solution of 4-(3-cyclopentyloxy- 4-methoxyphenyl)-4-hydroxy-3,4,5,6-tetrahydro- 2H-thiopyran (0.48 g; which is prepared as described in Example 1) in dry dichloromethane (100 mL) is treated with triethylsilane (8.4 mL), followed, dropwise, by trifluoroacetic acid (7.1 mL). The resulting pink solution is stirred at room temperature for 25 hours. The solution is washed with aqueous sodium bicarbonate solution (2×100 mL; 10% w/v) and the combined aqueous washings are extracted with dichloromethane (100 mL). The organic phases are combined and dried over sodium sulphate. After evaporation of the solvent the residue is subjected to flash chromatography on silica gel with toluene as eluent, to give a white solid (8.5 g). The solid is recrystallized from a mixture of pentane and ethyl acetate to give 4-( 3-cyclopentyloxy-4-methoxyphenyl)-3,4,5,6-tetrahydro-2H-thiopyran (3.8 g) in the form of a white solid, m.p. 83°–85° C. [Elemental analysis: C, 69.5; H,8.3; S,11.2%; calculated: C,69.8; H,8.3; S,11.0%].

EXAMPLE 3

Compounds B and G

A stirred suspension of sodium periodate (4.19 g) in water (25 mL) at 0° C. is treated with a solution of 4-( 3-cyclopentyloxy-4-methoxyphenyl)-4-hydroxy- 3,4,5,6-tetrahydro-2H-thiopyran (6 g; which is prepared as described in Example 1) in methanol (25 mL), and the resulting pasty mixture is stirred vigorously. Further quantities of water (20 mL) and methanol (20 mL) are added to aid stirring. After 8 hours, water (100 mL) and dichloromethane (100 mL) are added with vigorous stirring. The organic phase is separated and the aqueous layer is extracted with dichloromethane (3×100 mL). The combined dichloromethane phases are washed with water (100 mL) and dried over sodium sulphate. Evaporation of the solvent gives a white solid.

This solid is twice recrystallized from a mixture of ethyl acetate and methanol (9:1 v/v), to give 4-(3-cyclopentyloxy-4-methoxyphenyl)-t-4-hydroxy- 3,4,5,6-tetrahydro-2H-thiopyran r-1-oxide (2.67 g), in the form of a white solid, m.p. 148°–150° C. [Elemental analysis: c,62.5; H,7.4; S,9.9%; calculated: C,62.9; H,7.5; S,9.9%].

The mother liquors from the recrystallizations are evaporated and the residue is subjected to flash chromatography on silica gel, using a mixture of ethyl acetate and methanol (19:1 v/v) as eluent, to give 4-(3-cyclopentyloxy-4-methoxyphenyl)-c- 4-hydroxy-3,4,5,6-tetrahydro-2H-thiopyran r-1-oxide (2.67 g) in the form of a white solid, m.p. 141°–146° C. [Elemental analysis: C,63.0; H,7.6; S,9.9%].

EXAMPLE 4

Compound C

A solution of 4-(3-cyclopentyloxy- 4-methoxyphenyl)-4-hydroxy-3,4,5,6-tetrahydro- 2H-thiopyran (2.41 g; which is prepared as described in Example 1 in dichloromethane (25 mL) is treated with a solution of meta-chloroperbenzoic acid (4.04 g) in dichloromethane (50 mL) during a period of 1 hour, whilst maintaining the reaction mixture below 10° C. The reaction mixture is stirred for 3.5 hours at below 10% and then it is filtered and the filter-cake is washed with dichloromethane (100 mL). The combined organic layers are washed with aqueous potassium iodide solution (10 mL; 20% w/v), aqueous sodium thiosulphite solution (100 mL; 30% w/v) and saturated aqueous sodium bicarbonate (100 mL). The solution is dried over sodium sulphate and evaporated and the resulting residue is subjected to flash chromatography on silica gel, using a mixture of toluene and ethyl acetate (33:1 v/v) as eluent, to give 4-(3-cyclopentyloxy-4-methoxyphenyl)- 4-hydroxy-3,4,5,6-tetrahydro-2H-thiopyran 1,1-dioxide (1.04 g), in the form of a white solid, m.p. 147°–149° C. [Elemental analysis: C,60.5; H,7.3; S,9.5%; calculated: C,60.0; H,7.3; S,9.4%; NMR (CDCL$_3$): 1.56–1.68 (m,2H), 1.79–1.98 *m,6H), 2.21 (s, 1H), 2.63 (m,2H), 2.91 (m,2H), 3.57 (m,2H), 3.83 (s, 3H), 4.78 (m,1H), 6.83 (d,2H,J=8 Hz), 6.97 (dd,1H,J=8 Hz and J=3 Hz), 7.02 (d,1 H,J=3 Hz)].

EXAMPLE 5

Compound E

By proceeding in a manner similar to that described hereinbefore in Example 4, but using as starting material the appropriate quantity of 4-(3-cyclopentyloxy-4-methoxyphenyl)- 3,4,5,6-tetrahydro-2H-thiopyran (which is prepared as described in Example 2), there is prepared 4-(3-cyclopentyloxy-4-methoxyphenyl)- 3,4,5,6-tetrahydro-2H-thiopyran 1,1-dioxide (2.77 g) in the form of a white solid, m.p. 128°–130° C. [Elemental analysis: C,63.0; H,7.5; S,10.0%; calculated: C,62.9; H,7.5; S,9.9%].

EXAMPLE 6

Compounds F and H

A solution of 4-(3-cyclopentyloxy- 4-methoxyphenyl)-3,4,5,6-tetrahydro- 2H-thiopyran (6 g; which is prepared as described in Example 2) in methanol (90 mL) is treated with a solution of sodium periodate (4.4 g) in water (45 mL) during a period of 15 minutes, whilst cooling the reaction mixture in an ice bath to 0°–5° C. The reaction mixture is stirred for 22 hours whilst being allowed to warm to room temperature. It is then treated with water (150 mL) and dichloromethane (100 mL), and the mixture is vigorously stirred. The aqueous layer is separated and extracted with dichloromethane (3×100 mL). The combined organic layers are dried over sodium sulphate and the solvent is removed, to give an off-white solid.

This solid is twice recrystallized from a mixture of ethyl acetate and methanol (19:1 v/v), to give cis-4-( 3-cyclopentyloxy-4-methoxyphenyl)-3,4,5,6-tetrahydro- 2H-thiopyran 1-oxide (2.36 g), in the form of a white solid, m.p. 139+ –141° C. [Elemental analysis: C,66.6; H,7.9; S, 10.5%; calculated: C,66.2; H,7.8; S,10.4%].

The mother liquors from the recrystallization are evaporated, and the resulting residue is recrystallized from toluene, to give a second crop of cis-4-( 3-cyclopentyloxy-4-methoxyphenyl)-3,4,5,6-tetrahydro- 2H-thiopyran 1-oxide (0.4 g).

The toluene filtrate is evaporated and the residue is recrystallized from a mixture of ethyl acetate and pentane, to give a mixture of trans- 4-(3-cyclopentyloxy-4-methoxyphenyl)- 3,4,5,6-tetrahydro-2H-thiopyran 1-oxide and cis-4-(3-cyclopentyloxy-4-methoxyphenyl)- 3,4,5,6-tetrahydro-2H-thiopyran 1-oxide in the ratio of 22:3, (0.3 g) in the form of a white solid, m.p. 82°–85° C. [Elemental analysis: C,66.0; H,7.9; S,10.5%].

EXAMPLE 7

Compound I

By proceeding in a manner similar to that described hereinbefore in Example 1, but using as starting material the appropriate quantity of 3,4,5,6-tetrahydro- 2H-thiopyran-3-one, there is prepared 3-( 3-cyclopentyloxy-4-methoxyphenyl)-3-hydroxy- 3,4,5,6-tetrahydro-2H-thiopyran in the form of a white solid, m.p. 66°–67° C. (from a mixture of pentane and ethyl acetate). [Elemental analysis: C,66.2; H,7.9; S,10.5%; calculated: C,66.2; H,7.8; S,10.4%].

EXAMPLE 8

Compound J

By proceeding in a manner similar to that described hereinbefore in Example 2, but using as starting material the appropriate quantity of 3-(3-cyclopentyloxy-4-methoxyphenyl)- 3-hydroxy-3,4,5,6-tetrahydro-2H-thiopyran (which is prepared as described in Example 7), there is prepared 3-(3-cyclopentyloxy- 4-methoxyphenyl)-3,4,5,6-tetrahydro-2H-thiopyran in the form of white needles, m.p. 75°–77° C. (from pentane). [Elemental analysis: C,69.8; H,8.35: S,11.0%; calculated: C,69.8; H,8.27; S, 11.0%].

EXAMPLE 9

Compound K

By proceeding in a manner similar to that described hereinbefore in Example 4, but using as starting material the appropriate quantity of 3-(3-cyclopentyloxy-4-methoxyphenyl)- 3-hydroxy-3,4,5,6-tetrahydro-2H-thiopyran (which is prepared as described in Example 7), there is prepared 3-(3-cyclopentyloxy-4-methoxyphenyl)- 3-hydroxy-3,4,5,6-tetrahydro-2H-thiopyran 1,1-dioxide (2.94 g) in the form of a white solid, m.p. 145°–148° C. (from a mixture of toluene and ethyl acetate). [Elemental analysis: C,60.0; H,7.1; S,9.5%; calculated: C,60.0; H,7.1; S,9.4%].

EXAMPLE 10

Compounds L

By proceeding in a manner similar to that described hereinbefore in Example 4, but using as starting material the appropriate quantity of 3-(3-cyclopentyloxy-4-methoxyphenyl)- 3,4,5,6-tetrahydro-2H-thiopyran (which is prepared as described in Example 8), there is prepared 3-(3-cyclopentyloxy-4-methoxyphenyl)- 3,4,5,6-tetrahydro-2H-thiopyran 1,1-dioxide in the form of a white solid, m.p. 131°–132.5° C. [Elemental analysis: C,62.7; H,7.5; S,10.1%; calculated: C,62.9; H,7.5; S,9.9%].

EXAMPLE 11

Compounds M and N

By proceeding in a manner similar to that described hereinbefore in Example 3, but using as starting material the appropriate quantity of 3-(3-cyclopentyloxy-4-methoxyphenyl)- 3-hydroxy-3,4,5,6-tetrahydro-2H-thiopyran (which is prepared as described in Example 7), there is prepared, after evaporation of the dichloromethane extract, a foam.

This foam is subjected to flash chromatography on silica gel, using ethyl acetate, then a mixture of ethyl acetate and methanol (19:1 v/v), as eluents to give two components.

The first component is recrystallized from ethyl acetate, to give 3-(3-cyclopentyloxy-4-methoxyphenyl)-t- 3-hydroxy-3,4,5,6-tetrahydro-2H-thiopyran r-1-oxide, in the form of a white solid, m.p. 133°–134° C. [Elemental analysis: C,62.8; H,7.5; S,9.8%; calculated: C,62.9; H,7.5; S,9.9%].

The second component is chromatographed again on silica gel, using ethyl acetate as eluent, to give 3-(3-cyclopentyloxy- 4-methoxyphenyl)-c-3-hydroxy-3,4,5,6-tetrahydro- 2H-thiopyran r-1-oxide in the form of a white solid, m.p. 98°–100° C. [Elemental analysis: C,62.7; H,7.4; S,9.9%].

EXAMPLE 12

Compounds O and P

A solution of 3-(3-cyclopentyloxy- 4-methoxyphenyl)-3, 4,5,6-tetrahydro- 2H-thiopyran (6.2 g; which is prepared as described in Example 8) in methanol (100 mL) is treated with a solution of sodium periodate (4.58 g) in water (50 mL), during 30 minutes, whilst cooling in an ice bath to maintain the reaction mixture below 10° C. The mixture is stirred for 5 hours, and then it is allowed to stand at room temperature for 48 hours. The reaction mixture is then treated with water (160 mL) and dichloromethane (100 mL) and thoroughly stirred, and the phases are separated. The aqueous phase is extracted further with dichloromethane (3×100 mL) and the combined organic phases are dried over sodium sulphate and evaporated, to give a cream colored solid (6.6 g).

This solid is recrystallized from a mixture of ethyl acetate and methanol (19:1 v/v), to give a white solid (2.4 g), which is further subjected to flash chromatography on silica gel, using a mixture of ethyl acetate and methanol (19:1 v/v) as eluent, to give trans-3-( 3-cyclopentyloxy-4-methoxyphenyl)- 3,4,5,6-tetrahydro-2H-thiopyran 1-oxide (1.34 g) in the form of a white solid, m.p. 133°–134° C. [Elemental analysis: C,66.1; H,7.8; S,10.7%; calculated: C,66.1; H,7.8; S,10.4%].

The residues from the recrystallization and mixed fractions from the chromatography are combined and subjected to flash chromatography on silica gel, using a mixture of ethyl acetate and methanol (19:1 v/v) as eluent, to give a cream colored solid (1.52 g), which is recrystallized from a mixture of ethyl acetate and methanol (19:1 v/v), to give cis-3-( 3-cyclopentyloxy-4-methoxyphenyl)-3,4,5,6-tetrahydro- 2H-thiopyran 1-oxide (0.7 g), in the form of a white solid, m.p. 110°–111° C. [Elemental analysis: C,65.9; H,7.8; S,10.3%].

EXAMPLE 13

Compounds Q and R

By proceeding in a manner similar to that described hereinbefore in Example 4, but using as starting material the appropriate quantity of 3-(3-cyclopentyloxy-4-methoxyphenyl)- 3-hydroxytetrahydrothiophene (which is prepared as described in Example 14), there are prepared: 3-(3-cyclopentyloxy-4-methoxyphenyl)- 4,5-dihydrothiophene 1,1-dioxide, in the form of a white solid, m.p. 178°–179° C. [Elemental analysis: C,62.50; H,6.62; S,10.6%; calculated: C,62.32; H,6.54; S, 10.4%], and 3-(3-cyclopentyloxy-4-methoxyphenyl)-3-hydroxytetrahydrothiophene 1,1-dioxide, in the form of a white solid, m.p. 147°–148° C. [Elemental analysis: C,59.10; H,6.94; S,9.9%; calculated: C,58.88; H,6.79; S,9.82%].

EXAMPLE 14

Compound AB

A stirring suspension of magnesium turnings (3.45 g) in dry tetrahydrofuran (60 mL) is treated with 1,2-dibromoethane (0.8 mL), and the mixture is stirred under a nitrogen atmosphere for 30 minutes. It is then treated dropwise with a solution of 4-bromo- 2-cyclopentyloxyanisole (25 g); which is prepared as described in Reference Example 4 in tetrahydrofuran (20 mL), and the resulting solution is heated at reflux for 30 minutes. The solution is then cooled to room temperature and treated with a solution of tetrahydrothiophen- 3-one (6.9 mL) in tetrahydrofuran (20 mL), and allowed to stand for 16 hours. It is then treated with saturated aqueous ammonium chloride solution (50 mL), and the mixture is partitioned between water (100 mL) and dichloromethane (100 mL). The aqueous phase is further extracted with dichloromethane (100 mL). The combined organic phases are dried over magnesium sulphate and evaporated. The resulting residue is subjected to flash chromatography on silica gel, using a mixture of ethyl acetate and toluene as eluent to give 3-(3-cyclopentyloxy-4-methoxyphenyl)- 3-hydroxytetrahydrothiophene, in the form of a viscous oil.

EXAMPLE 15

Compound S

A stirred solution of 3-(3-cyclopentyloxy- 4-methoxyphenyl)-4,5-dihydrothiophene 1,1-dioxide (1.2 g; which is prepared as described in Example 13) in ethanol (50 mL) is treated with sodium borohydride (0.45 g) followed by cobalt dichloride hexahydrate (0.94 g), and the purple mixture is stirred at room temperature for 6 hours. It is then filtered through a pad of diatomaceous earth, and the pad is washed with dichloromethane (150 mL). The combined flitrate and washings are evaporated, and the resulting residue is subjected to flash chromatography on silica gel, using a mixture of ethyl acetate and toluene as eluent, to give an oil which slowly crystallizes. It is recrystallized from ethyl acetate at −40° C., to give 3-(3-cyclopentyloxy- 4methoxyphenyl)tetrahydrothiophene 1,1-dioxide (0.74 g) in the form of a white solid, m.p. 89°–90° C. [Elemental analysis: C, 61.8; H,7.10; S,10.4%; calculated: C,61.91; H,7.1; S,10.33%].

EXAMPLE 16

Compounds T and U

A solution of 3-(3-cyclopentyloxy- 4-methoxyphenyl)-t-3-hydroxy-3,4,5,6-tetrahydro- 2H-thiopyran r-1-oxide (3.4 g; which is prepared as described in Example 11) in acetonitrile (100 mL) is treated with para-toluenesulphonic acid (0.3 g) and the mixture is heated at reflux for 4.5 hours. The mixture is cooled, and the solvent is evaporated, to give an oil, which is partitioned between water (100 mL) and dichloromethane (100 mL). The organic phase is separated and the solvent is removed. The resulting residue is subjected to flash chromatography on silica gel, using a mixture of ethyl acetate and methanol (19:1 v/v) as eluent, to give two fractions.

The first fraction is recrystallized from a mixture of ethyl acetate and pentane and then from ethyl acetate, to give 3-(3-cyclopentyloxy-4-methoxyphenyl)-5,6-dihydro- 2H-thiopyran 1-oxide (0.96 g) in the form of a white solid, m.p. 92°–93° C. [Elemental analysis: C,66.2; H,7.3; S,10.3%; calculated: C,66.64; H,7.24; S,10.46%].

The second fraction is recrystallized from a mixture of ethyl acetate and pentane and chromatographed on silica gel, using ethyl acetate as eluent, to give a gum which is triturated with a mixture of ethyl acetate and pentane, to give 3-(3-cyclopentyloxy-4-methoxyphenyl)- 5,6-dihydro-4H-thiopyran 1-oxide (0.43 g) in the form of a white solid, m.p. 96–98° C. [Elemental analysis: C,66.4; H,7.2; S,10.0%].

EXAMPLE 17

Compounds V and W

By proceeding in a manner similar to that described hereinbefore in Example 16, but using as starting material the appropriate quantity of 3-(3cyclopentyloxy-4-methoxyphenyl)- 3-hydroxy-3,4,5,6-tetrahydro-2H-thiopyran 1,1-dioxide (which is prepared as described in Example 9), there are prepared: 3-(3-cyclopentyloxy-4-methoxyphenyl)- 5,6-dihydro-2H-thiopyran 1,1-dioxide in the form of white needles, m.p. 122°–124° C. (from ethyl acetate). [Elemental analysis: C,63.2; H,6.87; S,9.8%; calculated: C,63.33; H,6.88; S,9.94%] and 3-(3-cyclopentyloxy- 4-methoxyphenyl)-5,6-dihydro-4H-thiopyran 1,1-dioxide in the form of a white solid, m.p. 147°–149° C. [Elemental analysis: C,63.3; H,6.87; S,9.8%].

EXAMPLE 18

Compounds Y and Z

By proceeding in a manner similar to that described hereinbefore in Example 16, but using as starting material the appropriate quantity of 3-(3-cyclopentyloxy-4-methoxyphenyl)- 3-hydroxytetrahydrothiophene 1-oxide (which is prepared as described in Example 19), there are prepared: 3-(3-cyclopentyloxy-4-methoxyphenyl)- 2,5-dihydrothiophene 1-oxide n the form of a white solid, m.p. 127°–128° C. [Elemental analysis: C,65.5; H,6.89; S,10.9%; calculated: C,65.72; H,6.89; S,10.96%], and 3-(3-cyclopentyloxy-4-methoxyphenyl)- 4,5-dihydrothiophene 1-oxide in the form of a white solid, m.p. 128°–129° C. [Elemental analysis: C,65.2; H,6.87; S,10.8%].

EXAMPLE 19

Compound AC

By proceeding in a manner similar to that described hereinbefore in Example 3, but using as starting material the appropriate quantity of 3-(3-cyclopentyloxy-4-methoxyphenyl)- 3-hydroxytetrahydrothiophene (which is prepared as described in Example 14), there is prepared 3-(3-cyclopentyloxy- 4-methoxyphenyl)-3-hydroxytetrahydrothiophene 1-oxide [elemental analysis: C,61.9; H,7.2; S,10.4%; calculated: C,61.91; H,7.14; S,10.33%].

EXAMPLE 20

Compounds X and AD

A solution of 3-(3-cyclopentyloxy- 4-methoxyphenyl)tetrahydrothiophene (2.89 g); which is prepared as described in Example 21 in methanol (50 mL) is treated with a solution of sodium periodate (2.14 g) in water (25 mL) during 30 minutes whilst maintaining the reaction temperature below 10° C. The mixture is stirred for 4 hours and then it is allowed to stand at room temperature overnight. The reaction mixture is then partitioned between water (80 mL) and dichloromethane (50 mL), and the aqueous phase is further extracted with dichloromethane (3×50 mL). The combined extracts are evaporated and the resulting residue is subjected to flash chromatography on silica gel, using a mixture of ethyl acetate and methanol (9:1 v/v) as eluent, to give a mixture of cis- and trans-3-(3-cyclopentyloxy- 4-methoxyphenyl)tetrahydrothiophene 1-oxide in the form of a syrup (2.82 g).

A portion of this syrup (0.5 g) is further purified by high pressure liquid chromatography on silica gel, eluting with a mixture of heptane, isopropanol, methanol and triethylamine (90:8:2:0.25 v/v), to give: 3-(3-cyclopentyloxy-4-methoxyphenyl)tetrahydrothiophene 1-oxide (it is thought to be the cis-isomer, (0.21 g) in the form of a white solid, m.p. 66°–67° C. [Elemental analysis: C,65.40; H,7.70; S,10.80%; calculated: C,65.28; H,7.53; S,10.89%. NMR ($C_6D_6$): 7.07 (d,1H,J=2 Hz), 6.72 (dd,1H,$J_1$=8 Hzz, $J_2$=2 Hz), 6.50 (d,1H, J=8 Hz), 4.56 (m,1H), 3.43 (s,3H), 2.81 (dd, 1H,$J_1$=14 Hz,$J_2$=8 Hz), 2.68–2.49 (m,4H), 2.00–1.90 (m,3H), 1.81–1.63 (m,5H), 1.46–1.33 (M,2H)], and 3-( 3-cyclopentyloxy-4-methoxyphenyl)tetrahydrothiophene 1-oxide (it is thought to be the trans-isomer, (0.15 g) in the form of a white solid, m.p. 78°–80° C. [Elemental analysis: C,64.70; H,7.50; S,10.50%. NMR ($C_6D_6$): 6.56 (d,1H,J=8 Hz), 6.55 (d,1H, J=2 Hz), 6.42 (dd,1H,$J_1$=8 Hz,$J_2$=2 Hz), 4.57 (m,1H), 3.89 (m,1H), 3.40 (s,3H), 2.89 (dd, 1H,$J_1$=14 Hz,$J_2$=6 Hz), 2.66 (ddd,1H,$J_1$=14 Hz,$J_2$=10 Hz,$J_3$ =4 Hz), 2.38 (m,1H), 2.15 (m,1H), 2.01–1.85 (m,3H), 1.82–1.70 (m,2H), 1.65–1.54 (m,2H), 1.47–1.24 (m,3H)].

EXAMPLE 21

Compound AE

A solution of 3-(3-cyclopentyloxy- 4-methoxyphenyl)-3-hydroxytetrahydrothiophene (2.94 g; which is prepared as described in Example 14) and triethylsilane (2.7 mL) in dichloromethane (30 mL) under a nitrogen atmosphere is treated with trifluoroacetic acid (2.3 mL) during 15 minutes. The mixture is stirred for 3.5 hours and then it is allowed to stand for 2 days. The mixture is diluted with dichloromethane (150 mL) and the solution is washed with saturated aqueous sodium bicarbonate solution (2×25 mL), brine (2×25 mL) and water (2×25 mL). The solution is dried over magnesium sulphate, the solvent is removed and the oily residue is subjected to flash chromatography, using a mixture of pentane and ethyl acetate (19:1 v/v) as eluent, to give 3-(3-cyclopentyloxy- 4-methoxyphenyl)tetrahydrothiophene (1.34 g) in the form of a pale yellow oil.

EXAMPLE 22

Compound AA

By proceeding in a manner similar to that described in Example 6 but using as starting material the appropriate quantity of 3-( 3-cyclopentyloxy-4-methoxyphenyl)-3-methoxy- 3,4,5,6-tetrahydro-2H-thiopyran (which is prepared as described in Example 23), there is prepared, after flash chromatography on silica gel, using a mixture of ethyl acetate and methanol (90:1 v/v) as eluent, a mixture of isomers of 3-(3-cyclopentyloxy- 4-methoxyphenyl)-3-methoxy- 3,4,5,6-tetrahydro-2H-thiopyran 1-oxide in the form of a colorless oil. [Elemental analysis: C,61.2; H,7.9; S,9.00; $H_2O$, 3.5%; calculated for $C_{18}H_{26}O_4S$: 0.75 $H_2O$: C,61.42; H,7.87; S,9.11; $H_2O$,3.8%].

EXAMPLE 23

Compound AF

A solution of 3-(3-cyclopentyloxy- 4-methoxyphenyl)-3-hydroxy-3,4,5,6-tetrahydro- 2H-thiopyran (2 g; which is prepared as described in Example 7) methanol (175 mL) is treated with trifluoroacetic acid (0.5 mL) and the mixture is allowed to stand at room temperature overnight. The mixture is concentrated in vacuo, and it is then treated with diethyl ether (175 mL) and washed with saturated aqueous sodium bicarbonate solution (25 mL) and water (25 mL) and dried over magnesium sulphate. The solvent is removed and the resulting oily residue is subjected to flash chromatography on silica gel, using a mixture of pentane and ethyl acetate (9:1 v/v) as eluent, to give 3-(3-cyclopentyloxy-4-methoxyphenyl)- 3-methoxy-3,4,5,6-tetrahydro-2H-thiopyran (1.16 g), in the form of a colorless oil.

EXAMPLE 24

Compounds XA and XB 3-(3-Cyclopentyloxy- 4-methoxphenyl)tetrahydrothiophene 1-oxide (compound X, which is prepared as described in Example 20 and thought to be cis-3-(3-cyclopentyloxy- 4-methoxphenyl)tetrahydrothiophene 1-oxide) is resolved by HPLC (high pressure liquid chromatography) on a chiral column (using Chiralcel OD, purchased from Daicel, as the stationary phase) and eluting with a mixture of hexane, methanol and isopropanol ( 10:3:2 v/v) into its enantiomers, it is thought to be: (+)-cis-3-( 3-cyclopentyloxy-4methoxphenyl)tetrahydrothiophene 1-oxide; and (–)-cis-3-(3-cyclopentyloxy- 4-methoxphenyl)tetrahydrothiophene 1-oxide.

EXAMPLE 25

Compounds AG and AH

A solution of 3-(3-cyclopentyloxy- 4-methoxyphenyl)tetrahydrothiophene 1-oxide (0.2 g; compound XA, which is prepared as described in Example 24 and thought to be (+)-cis-3-(3-cyclopentyloxy- 4-methoxphenyl)tetrahydrothiophene 1-oxide) in methanol (5 mL) is treated with a solution of potassium peroxymonosulphate (0.3 g) in water (5 mL). After warming to room temperature and stirring for 3 hours, the mixture is allowed to stand overnight. It is then treated with water (40 mL) and extracted with dichloromethane (3×15 mL). The combined extracts are washed with brine (15 mL), dried over magnesium sulphate, anti evaporated, to give (+)-cis-3-( 3-cyclopentyloxy-4-methoxyphenyl)tetrahydro-thiophene 1,1-dioxide (0.14 g) in the form of a pale yellow gum, $^{22}[\alpha]_D$=+13.1° (dichloromethane). [Elemental analysis: C,62.2; H,7.6; S,9.7%; calculated: C,61.9; H,7.1; S,10.3%].

By proceeding in a similar manner, but using the other isomer compound XB, there is prepared (–)-3-( 3-cyclopentyloxy-4-methoxphenyl)tetrahydrothiophene 1,1-dioxide in the form of a pale yellow gum, $^{22}[\alpha]_D$=–12.5° (dichloromethane). [Elemental analysis: C,62.5; H,7.4; S,9.9%].

REFERENCE EXAMPLE 1

A stirred, ice-cold, aqueous solution of sodium hydroxide (250 mL; 15% w/v) is treated, dropwise, with guaiacol (22 mL), followed by benzoyl chloride (25.5 mL), and the mixture is stirred for a further period of 40 minutes. The resulting crystalline white solid is filtered off, washed with water, and dried, to give 2-methoxyphenyl benzoate (29.2 g), m.p. 59°–60° C. [Elemental analysis: C,73.3; H,5.2%; calculated: C,73.7; H, 5.3%].

REFERENCE EXAMPLE 2

A stirred solution of 2-methoxyphenyl benzoate (29.1 g) in glacial acetic acid (150 mL) is treated with a solution of bromine (7.2 mL) in glacial acetic acid (25 mL) during a period of 20 minutes, and the solution is then stirred for a further period of 30 minutes at room temperature. The mixture is concentrated in vacuo, and the resulting residue is dissolved in methyl t-butyl ether (200 mL), washed with water (100 mL) and saturated aqueous sodium bicarbonate solution (3×100 mL), dried over magnesium sulphate and evaporated. The resulting residue is recrystallized from cyclohexane, to give 4-bromo-2-methoxyphenyl benzoate (22.7), m.p. 73°–75° C. [Elemental analysis: C,55.0; H,3.6; Br, 25.5%; calculated: C,54.6; H,3.9; Br, 25.9%].

REFERENCE EXAMPLE 3

A mixture of 4-bromo-2-methoxyphenyl benzoate (5 g), sodium hydroxide (3 g), water (5 mL) and ethanol (50 mL) is heated at reflux for 1.5 hours. It is then evaporated to low bulk and the resulting residue is treated with water (20 mL) and concentrated hydrochloric acid (10 mL), and extracted with dichloromethane (150 mL). The organic solution is extracted with saturated aqueous sodium bicarbonate solution (3×25 mL), dried over magnesium sulphate and evaporated, to give 5-bromo-2-methoxyphenol (3.25 g), in the form a colorless solid, m.p. 67°–68° C. [Elemental analysis: C,41.5; H,3.5; Br, 37.8%; calculated: C,41.6; H,3.5; Br, 39.5%].

REFERENCE EXAMPLE 4

A solution of 5-bromo-2-methoxyphenol (74 g), cyclopentyl bromide (80.5 g) and potassium carbonate (73.6 g) in dimethylformamide (500 mL) is stirred at 60° C. for 16 hours. It is then concentrated and the resulting residue is treated with water (250 mL). This mixture is then extracted with dichloromethane (3×250 mL) and the combined extracts are dried over magnesium sulphate, and evaporated, to give 4-bromo- 2-cyclopentyloxyanisole (95.5 g) in the form of a pale brown liquid. [NMR ($CDCl_3$): 1.56–1.68 (m,2H), 1.77–1.99 (m,6H), 3.81 (s,3H), 4.71–4.75 (m,1H), 6.72 (d,1H), 6.98 (d,1H), 7.00 (dd, 1H)].

The compounds of formula I exhibit useful pharmacological activity and accordingly may be incorporated into pharmaceutical compositions and used in the treatment of patients suffering from certain medical disorders. More especially, they are cyclic AMP phosphodiesterase inhibitors, in particular type IV cyclic AMP phosphodiesterase inhibitors. The present invention provides compounds of formula I, and compositions containing compounds of formula I, which are of use in a method for the treatment of a patient suffering from, or subject to, conditions which can be ameliorated by the administration of an inhibitor of cyclic AMP phosphodiesterase. For example, compounds within the present invention are useful as bronchodilators and asthma-prophylactic agents and agents for the inhibition of eosinophil accumulation and of the function of eosinophils, e.g. for the treatment of inflammatory airways disease, especially reversible airway obstruction or asthma, and for the treatment of other diseases and conditions characterized by, or having an etiology involving, morbid eosinophil accumulation. As further examples of conditions which can be ameliorated by the administration of inhibitors of cyclic AMP phosphodiesterase such as compounds of general formula I there may be mentioned inflammatory diseases, such as atopic dermatitis, urticaria, allergic rhinitis, psoriasis, rheumatic arthritis, ulcerative colitis, Crohn's disease, adult respiratory distress syndrome and diabetes insipidus, other proliferative skin diseases such as keratosis and various types of dermatitis, conditions associated with cerebral metabolic inhibition, such as cerebral senility, multi-infarct dementia, senile dementia (Alzheimer's disease), and memory impairment associated with Parkinson's disease, and conditions ameliorated by neuroprotectant activity, such as cardiac arrest, stroke, and intermittent claudication. A special embodiment of the therapeutic methods of the present invention is the treating of asthma.

The compounds are also inhibitors of tumor necrosis factor, especially α-TNF. Thus, the present invention provides compounds of formula I, and compositions containing compounds of formula I, which are of use in a method for treating a patient suffering from, or subject to, conditions which can be ameliorated by the administration of an inhibitor of α-TNF. For example compounds of the present invention are useful in joint inflammation, arthritis, rheumatoid arthritis and other arthritic conditions such as rheumatoid spondylitis and osteoarthritis. Additionally, the compounds are useful in treatment of sepsis, septic shock, gram negative sepsis, toxic shock syndrome, acute respiratory distress syndrome, asthma and other chronic pulmonary diseases, bone resorption diseases, reperfusion injury, graft vs host reaction and allograft rejection. Furthermore, the compounds are useful in the treatment of infections such as viral infections and parasitic infections, for example malaria such as cerebral malaria, fever and myalgias due to infection, HIV, AIDS, cachexia such as cachexia secondary to AIDS or to cancer. Other disease states that may be treated with the compounds of the present invention include Crohn's disease, ulcerative colitis, pyresis, systemic lupus erythematosus, multiple sclerosis, type I diabetes mellitus, psoriasis, Bechet's disease, anaphylactoid purpura nephritis, chronic glomerulonephritis, inflammatory bowel disease and leukemia. A special embodiment of the therapeutic methods of the present invention is the treating of joint inflammation.

According to a further feature of the invention there is provided a method for the treatment of a human or animal patient suffering from, or subject to, conditions which can be ameliorated by the administration of an inhibitor of cyclic AMP phosphodiesterase or of TNF, especially α-TNF, for example conditions as hereinbefore described, which comprises the administration to the patient of an effective amount of compound of formula I or a composition containing a compound of formula I. "Effective amount" is meant to describe an amount of compound of the present invention effective in inhibiting cyclic AMP phosphodiesterase and/or TNF and thus producing the desired therapeutic effect.

The present invention also includes within its scope pharmaceutical formulations which comprise at least one of the compounds of formula I in association with a pharmaceutically acceptable carrier or coating.

In practice compounds of the present invention may generally be administered parenterally, rectally or orally, but they are preferably administered by inhalation.

The products according to the invention may be presented in forms permitting administration by the most suitable route and the invention also relates to pharmaceutical compositions containing at least one product according to the invention which are suitable for use in human or veterinary medicine. These compositions may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of tablets. pills, granules, powders, aqueous solutions or suspensions, injectable solutions, elixirs or syrups, and can contain one or more agents chosen from the group comprising sweeteners, flavorings, colorings, or stabilizers in order to obtain pharmaceutically acceptable preparations.

The choice of vehicle and the content of active substance in the vehicle are generally determined in accordance with the solubility and chemical properties of the product, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulphate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

For parenteral administration, emulsions, suspensions or solutions of the products according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilized by heating, irradiation or microfiltration.

Suitable compositions containing the compounds of the invention may be prepared by conventional means. For example, compounds of the invention may be dissolved or suspended in a suitable carrier for use in a nebulizer or a suspension or solution aerosol, or may be absorbed or adsorbed onto a suitable solid carrier for use in a dry powder inhaler.

Solid compositions for rectal administration include suppositories formulated in accordance with known methods and containing at least one compound of formula I.

The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.001 to about 50, preferably about 0.001 to about 5, mg/kg body weight per day by inhalation, from about 0.01 to about 100, preferably 0.1 to 70, more especially 0.5 to 10, mg/kg body weight per day by oral administration, and from about 0.001 to about 10, preferably 0.01 to 1, mg/kg body weight per day by intravenous administration. In each particular case, the doses will be determined in accordance with the factors distinctive to the subject to be treated, such as age, weight, general state of health and other characteristics which can influence the efficacy of the medicinal product.

The products according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. It goes without saying that, for other patients, it will be necessary to prescribe not more than one or two doses per day.

Compounds within the scope of the present invention exhibit marked pharmacological activities according to tests described in the literature which tests results are believed to correlate to pharmacological activity in humans and other mammals. The following pharmacological test results are typical characteristics of compounds of the present invention.

Partial purification of pig aortic PDE IV

Aortas of freshly slaughtered pigs are clamped with artery forceps, excised, rinsed with water and placed in Hepes-buffered Krebs solution (118 mM NaCl, 4.7 mM KCl, 2.5 mM $CaCl_2$, 1.6 mM $MgSO_4$, 1.2 mM $KH_2PO_4$, 5.6 mM glucose, 2 mM Hepes. pH 7.4) for transport from the abattoir back to the laboratory. Within 2 hours of removal, the aortas are placed on a plastic dissecting mat, any extraneous tissue is trimmed from the outside of the aorta and the artery is cut lengthwise through the thoracic arterial stumps. The artery is then pinned out with syringed needles and excell blood is removed by suction. The endothelial layer is removed by rubbing the intimal surface of the artery with a cotton swab. A criss-cross pattern is cut into the smooth muscle to a depth of 3–4 mm using a scalpel blade. The resulting rectangular strips of smooth muscle are then plucked from the aorta and washed (Krebs solution) and blotted dry. Then 25 g of the smooth muscle strips are cut finely with sharp scissors and homogenized using a Waring Blender (3×35 s bursts) in 50–100 ml of an ice-cold solution of 20 mM-Tris/HCl (pH 7.5), 2 mM $MgCl_2$, 1 mM dithiothreitol, 5 mM EDTA and 1 mg/ml aprotinin. The homogenate is transferred to 50 ml centrifuge tubes and further homogenized on ice using an Ultra-Turrax homogenizer. The homogenate is centrifuged (3000 g, 5 min). After removal of the supernatant, the pellet is sonicated (45×10 sat 20 s intervals) in a small volume (25–50 ml) of homogenization buffer. The sonicate is then centrifuged (3000 g, 5 min), the pellet discarded and the supernatant pooled with that from the first centrifugation step. The pooled supernatants are centrifuged at high speed (100,000 g, 1 hour, 4° C.). The resultant supernatant (75–150 ml) is filtered (0.45 pm) and protein determined before application to a column (50 cm×2.44 cm)of DEAE-trisacryl (IBF, Villeneuve La Garenne, France) pre-equilibrated with the same column buffer (without deoxycholate) as used for partial purification of solubilized eosinophil PDE IV. The column is washed with 500–700 ml of column buffer, and PDE activities are eluted with two successive linear gradients of NaCl (0–200 mM, 400 ml and 200–300 mM, 200 ml) in column buffer. The flow rate throughout is 1 ml/min and 7 ml fractions are collected and assayed for long-term storage at −20° C. ethylene glycol is added to a final concentration of 30% (v/v). Activity is stable for several weeks under these conditions.

Measurement of PDE activity

PDE activity is determined by the two-step radioisotopic method of Thompson et al., *Adv. Cyclic Nuc. Res.,* 10, 69–92 ( 1979). The reaction mixture contained 20 mM Tris/HCl (pH 8.0), 10 mM $MGCl_2$, 4 mM 2-mercaptoethanol, 0.2 mM EGTA and 0.05 mg of BSA/ml. Unless otherwise stated, the concentration of substrate is 1 μM.

The $IC_{50}$ values for the compounds examined are determined from concentration-response curves in which concentrations ranged from 0.6 to 1 mM. A least three concentration-response curves are generated for each agent.

Compounds within the scope of the invention produce up to about 50% inhibition of porcine aorta cyclic AMP phosphodiesterase IV at concentrations from about $10^{-9}$M up to about $10^{-5}$M. The compounds of the invention are from about 300-fold to about 50-fold more selective for cyclic AMP phosphodiesterase IV than cyclic AMP phosphodiesterase I, III or V.

Compounds within the scope of the invention produce up to about 50% relaxation of guinea-pig tracheal strips, which had been contracted by treatment with spasmogens such as histamine and carbachol, at concentrations from about $10^{-7}$M to about $10^{-4}$M.

Preparation of guinea-pig eosinophils

Male Dunkin-Hartley guinea pigs (250–400 g) are injected (intraperitoneally) with 0.5 ml of donor horse serum twice weekly. At least 5 days after the second injection, the guinea pigs are killed by $CO_2$ asphyxiation. A ventral incision is made and 30 ml of Hanks buffered salt solution (HBSS) with $Ca^{2+}$ (Gibco, U.K. Ltd., Uxbridge, Middx., U.K.) poured into the abdominat cavity. The abdomen is gently massaged for approximately 1 min; a ventral incision is then made and the peritoneal exudate is aspirated and centrifuged at 250 g for 10 minutes at 4° C. The supernatant is discarded and the pellet washed once (10 ml of HBSS) and resuspended in HBSS. Portions (1 ml) of the cell suspension are layered on to a discontinuous (18.5% and 22.5%, w/v) metrizamide gradient prepared in conical tubes by dissolving metrizamide in Tyrodes buffer (137 mM NaCl, 2.7 mM KCl, 11.9 mM $NaHCO_3$, 0.35 mM $Na_2HPO_4$, 5.5 mM glucose, pH 7.3) containing 0.1% gelatin. The gradients are centrifuged (250 g, 20 minutes, 20° C.) and the eosinophil-rich cell pellet is resuspended in 10 ml of HBSS. Total cell counts are determined using a Coulter counter and differential cell counts obtained from cytospin slides fixed in methanol and stained with Wright-Giemsa. Cell viability, as determined by Trypan Blue exclusion, is greater than 99% and eosinophil purity greater than 97%.

Compounds within the scope of the invention inhibit by up to about 50% the accumulation of eosinophils in the lungs of guinea-pigs at intraperitoneal doses from about 1 to about 25 mg/kg or at oral doses from about 1 to about 50 mg/kg.

Compounds within the scope of the invention produce up to about 50% inhibition of superoxide generation from eosinophils harvested from the peritoneal cavities of guinea-pigs at concentrations from about $10^{-8}$M to about $10^{-5}$M.

Bronchorelaxant activity is measured in in vivo tests in the anaesthetized guinea-pig according to the method of Dixon and Brodie [J. Physiol., 29, 97–173, (1903)] in which the effects on histamine-induced bronchospasm and mean arterial blood pressure are determined. Nebulized aerosols generated from aqueous solutions of compounds of the invention are each administered for one; minute to the anaesthetized guinea-pigs. Alternatively, dry powder formulations made up from compounds of the invention and lactose are blown into the airways of the anaesthetized guinea-pigs.

Compounds within the scope of the invention produce from about 30% up to about 90% decrease in bronchospasm when administered at effective doses of about 20–80 µg, without any significant effect on blood pressure.

Compounds within the scope of the invention, administered one hour before challenge, inhibit by at least 50% ovalbumin-induced eosinophilia in guinea-pigs which is measured 24 hours after challenge, at oral doses of about 1 to about 50 mg/kg.

Compounds within the scope of the invention administered 1 hour before challenge inhibit by up to about 50% ovalbumin- or PAF-included hyperactivity in guinea-pigs at oral doses from about 1 to about 50 mg/kg.

Compounds within the scope of the invention inhibit PAF or ovalbumin-induced microvascular leakage (which is measured using flourescein isothiocyanate dextran) by up to 100% in guinea-pigs when administered at doses of about 1 to about 50 mg/kg orally or parenterally or at doses of about 20 to about 500 µg intratracheally.

The compounds within the scope of the invention inhibit in vitro α-TNF production by human monocytes derived from normal human blood donors. The $IC_{50}$ figures are found to be between 1000 nM and 10 nM or even less.

The value of the compounds of the invention is enhanced by their very low mammalian toxicity levels.

The following Composition Example illustrates pharmaceutical compositions according to the present invention.

COMPOSITION EXAMPLE 1

3-(3-Cyclopentyloxy- 4-methoxyphenyl)tetrahydrothiophene 1-oxide (compound X, thought to be the cis-isomer) (1 g)(mean particle size 3.5 microns) and lactose (99 g); (mean particle size 72 microns) are blended together for 30 minutes in a mechanical shaker/mixer. The resulting blend is filled, to a fill weight of 25 mg, into No. 3 hard gelatin capsules, to give a product suitable for use, for example, with a dry powder inhaler.

Similar compositions are prepared using other compounds of formula I.

The present invention may be embodied in other specific forms without departing from the spirit or essential attributes thereof and, accordingly, reference should be made to the appended claims, rather than the specification, as indicating the scope of the invention.

What is claimed is:

1. 1-Alkoxy-2-(alkoxy- or cycloalkyloxy-)- 4-(cyclothioalkyl- or cyclothioalkenyl-)benzene.

2. A compound of formula I

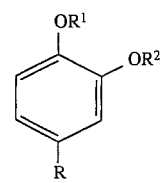

formula I wherein
 $R^1$ is alkyl;
 $R^2$ is alkyl or cycloalkyl group; and
 R is cyclothioalkyl or cyclothioalkenyl.

3. The compound of claim 2 wherein said cyclothioalkyl is a group according to one of the following formulae:

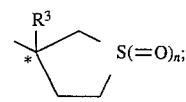

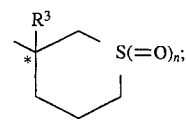

and

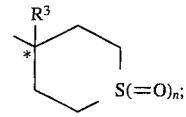

wherein:
 $R^3$ is hydrogen, lower alkyl, lower alkoxy, hydroxyl, acyloxy or aroyloxy; and
 n is 0 to 2.

4. The compound of claim 2 wherein said cyclothioalkenyl is a group according to one of the following formulae:

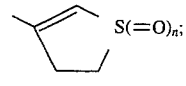

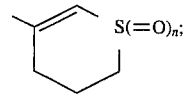

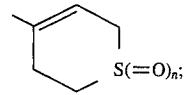

and

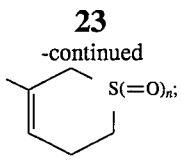

wherein:
n is 0 to 2.

5. The compound of claim 3 wherein $R^1$ is lower alkyl and $R^2$ is cycloalkyl of 5 to 7 ring atoms.

6. The compound of claim 3 wherein $R^3$ is a hydrogen, hydroxy group, lower alkyl or lower alkoxy.

7. The compound of claim 2 which is (A) 4-(3-cyclopentyloxy-4-methoxyphenyl)- 4-hydroxy-3,4,5,6-tetrahydro-2H-thiopyran;

(B) 4-(3-cyclopentyloxy-4-methoxyphenyl)-t- 4-hydroxy-3,4,5,6-tetrahydro- 2H-thiopyran r-1-oxide;

(C) 4-(3-cyclopentyloxy-4-methoxyphenyl)- 4-hydroxy-3,4,5,6-tetrahydro-2H-thiopyran 1,1-dioxide;

(D) 4-(3-cyclopentyloxy-4-methoxyphenyl)- 3,4,5,6-tetrahydro-2H-thiopyran;

(E) 4-(3-cyclopentyloxy-4-methoxyphenyl)- 3,4,5,6-tetrahydro-2H-thiopyran 1,1 -dioxide;

(F) cis-4-(3-cyclopentyloxy-4-methoxyphenyl)- 3,4,5,6-tetrahydro-2H-thiopyran 1-oxide;

(G) 4-(3-cyclopentyloxy-4-methoxyphenyl)-c- 4-hydroxy-3,4,5,6-tetrahydro- 2H-thiopyran r-1-oxide;

(H) trans-4-(3-cyclopentyloxy- 4-methoxyphenyl)-3,4,5,6-tetrahydro-2H-thiopyran 1-oxide;

(I) 3-(3-cyclopentyloxy-4-methoxyphenyl)- 3-hydroxy-3,4,5,6-tetrahydro-2H-thiopyran;

(J) 3-(3-cyclopentyloxy-4-methoxyphenyl)- 3,4,5,6-tetrahydro-2H-thiopyran;

(K) 3-(3-cyclopentyloxy-4-methoxyphenyl)- 3-hydroxy-3,4,5,6-tetrahydro-2H-thiopyran 1,1 -dioxide;

(L) 3-(3-cyclopentyloxy-4-methoxyphenyl)- 3,4,5,6-tetrahydro-2H-thiopyran 1,1-dioxide;

(M) 3-(3-cyclopentyloxy-4-methoxyphenyl)-t- 3-hydroxy-3,4,5,6-tetrahydro- 2H-thiopyran r-1-oxide;

(N) 3-(3-cyclopentyloxy-4-methoxyphenyl)-c- 3-hydroxy-3,4,5,6-tetrahydro- 2H-thiopyran r-1-oxide;

(O) trans-3-(3-cyclopentyloxy- 4-methoxyphenyl)-3,4,5,6-tetrahydro-2H-thiopyran 1-oxide;

(P) cis-3-(3-cyclopentyloxy-4-methoxyphenyl)- 3,4,5,6-tetrahydro-2H-thiopyran 1-oxide;

(Q) 3-(3-cyclopentyloxy-4-methoxyphenyl)- 4,5-dihydrothiophene 1,1-dioxide;

(R) 3-(3-cyclopentyloxy-4-methoxyphenyl)- 3-hydroxytetrahydrothiophene 1,1-dioxide;

(S) 3-(3-cyclopentyloxy- 4-methoxyphenyl)tetrahydrothiophene 1,1-dioxide;

(T) 3-(3-cyclopentyloxy-4-methoxyphenyl)- 5,6-dihydro-2H-thiopyran 1-oxide;

(U) 3-(3-cyclopentyloxy-4-methoxyphenyl)- 5,6-dihydro-4H-thiopyran 1-oxide;

(V) 3-(3-cyclopentyloxy-4-methoxyphenyl)- 5,6-dihydro-2H-thiopyran 1,1-dioxide;

(W) 3-(3-cyclopentyloxy-4-methoxyphenyl)- 5,6-dihydro-4H-thiopyran 1,1-dioxide;

(X) cis-3-(3-cyclopentyloxy- 4-methoxyphenyl)-tetrahydrothiophene 1-oxide;

(Y) 3-(3-cyclopentyloxy-4-methoxyphenyl)- 2,5-dihydrothiophene 1-oxide;

(Z) 3-(3-cyclopentyloxy-4-methoxyphenyl)- 4,5-dihydrothiophene 1-oxide;

(AA) 3-(3-cyclopentyloxy-4-methoxyphenyl)- 3-methoxy-3,4,5,6-tetrahydro- 2H-thiopyran 1-oxide;

(AB) 3-(3-cyclopentyloxy-4-methoxyphenyl)- 3-hydroxy-tetrahydrothiophene;

(AC) 3-(3-cyclopentyloxy-4-methoxyphenyl)- 3-hydroxytetrahydrothiophene 1-oxide;

(AD) trans-3-(3-cyclopentyloxy- 4-methoxyphenyl)tetrahydrothiophene 1-oxide;

(AE) 3-(3-cyclopentyloxy- 4-methoxyphenyl)tetrahydrothiophene;

(AF) 3-(3-cyclopentyloxy-4-methoxyphenyl)- 3-methoxy-3,4,5,6-tetrahydro- 2H-thiopyran;

(AG) (+)-3-(3-cyclopentyloxy- 4-methoxphenyl)tetrahydrothiophene 1,1-dioxide;

(AH) (−)-3-(3-cyclopentyloxy- 4-methoxphenyl)tetrahydrothiophene 1,1-dioxide;

(XA) (+)-cis-3-(3-cyclopentyloxy- 4-methoxphenyl)tetrahydrothiophene 1-oxide; or (XB) (−)-cis-3-(3-cyclopentyloxy- 4-methoxphenyl)tetrahydrothiophene 1-oxide.

8. A pharmaceutical composition comprising a compound of claim 1 and a pharmaceutically acceptable carrier.

9. A method for treating a disease state capable of being modulated by inhibiting production of cyclic AMP phosphodiesterase or TNF by administering to a patient suffering from said disease state an effective amount of the compound of claim 1.

10. The method of claim 9 wherein the disease state is an inflammatory disease or autoimmune disease.

11. The method of claim 10 wherein the disease state is selected from the group consisting of joint inflammation, arthritis, rheumatoid arthritis, rheumatoid spondylitis and osteoarthritis, sepsis, septic shock, gram negative sepsis, toxic shock syndrome, acute respiratory distress syndrome, asthma, bone resorption diseases, reperfusion injury, graft vs host reaction, allograft rejection malaria, myalgias, HIV, AIDS, cachexia, Crohn's disease, ulcerative colitis, pyresis, systemic lupus erythematosus, multiple sclerosis, type I diabetes mellitus, psoriasis, Bechet's disease, anaphylactoid purpura nephritis, chronic glomerulonephritis, inflammatory bowel disease and leukemia.

12. The method of claim 11 wherein the disease state is joint inflammation.

13. The method of claim 9 wherein the disease is a pathological condition attributable to increases in cyclic AMP phophodiesterase, eosinophil accumulation or the function of eosinophils.

14. The method of claim 13 wherein the pathological condition is asthma, atopic dermatitis, urticaria, allergic rhinitis, psoriasis, rheumatic arthritis, ulcerative colitis, Crohn's disease, adult respiratory distress syndrome, diabetes insipidus, keratosis, dermatitis, cerebral senility, multiinfarct dementia, senile dementia, memory impairment associated with Parkinson's disease, cardiac arrest, stroke and intermittent claudication.

15. The method of claim 14 wherein the pathological condition is asthma.

16. A process for preparing a compound of formula I of claim 2 comprising coupling of a compound of formula X

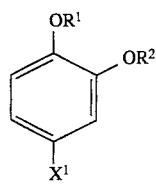

formula X wherein R¹ and R² are as defined above, and X¹ is a halo with a compound of formula XI

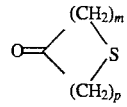

formula XI wherein m is 1 or 2 and p is 2 or 3, such that m+p=3 or 4.

17. The process of claim 16 further comprising reducing the compound of formula 1 wherein R³ is hydroxyl to a compound of formula 1 wherein R³ is hydrogen.

18. The process of claim 16 further comprising acylating the compound of formula 1 wherein R³ is hydroxyl to a compound of formula 1 wherein R³ is acyloxy or aroyloxy.

19. The process of claim 16 further comprising alkylating the compound of formula 1 wherein R³ is hydroxyl to a compound of formula 1 wherein R³ is lower alkoxy.

20. The process of claim 16 further comprising dehydrating the compound of formula 1 wherein R³ is hydroxyl to a compound of formula 1 wherein R is said cyclothioalkenyl selected from one of the following formulae:

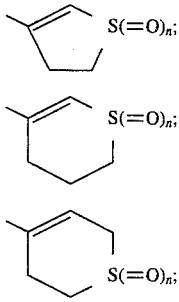

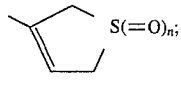

and

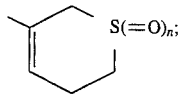

wherein n is 0 to 2.

21. The process of claim 16 further comprising oxidizing the product of claim 16.

22. The process of claim 20 further comprising oxidizing the product of claim 20.

23. A process for preparing a compound of formula I of claim 2 comprising reacting a compound of formula X

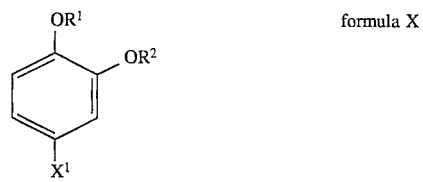

wherein R¹ and R² are as defined above, and X¹ is a halo with a compound of formula XII

wherein R³ is lower alkyl.

* * * * *